US006180402B1

(12) United States Patent
Granville et al.

(10) Patent No.: US 6,180,402 B1
(45) Date of Patent: *Jan. 30, 2001

(54) METHOD FOR INHIBITING APOPTOSIS INDUCED BY PHOTODYNAMIC THERAPY USING A CYSTEINE OR SERINE PROTEASE INHIBITOR

(75) Inventors: David J. Granville; Julia G. Levy; David W. C. Hunt, all of Vancouver (CA)

(73) Assignees: QLT Inc., Victoria; University of British Columbia, Vancouver, both of (CA)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/754,491

(22) Filed: Nov. 20, 1996

(51) Int. Cl.$^7$ .................................................. C12N 5/00

(52) U.S. Cl. ............................................................ 435/375

(58) Field of Search ........................ 435/1.1, 375; 514/2

(56) References Cited

U.S. PATENT DOCUMENTS

| 5,281,721 | 1/1994 | Powers et al. . |
| 5,464,833 | 11/1995 | Nakai et al. . |
| 5,500,432 | 3/1996 | Nicolaou . |
| 5,550,019 | 8/1996 | Reed . |
| 5,567,425 | 10/1996 | Bathurst et al. . |

FOREIGN PATENT DOCUMENTS

| WO 91/02540 | 3/1991 | (WO) . |
| 94/00154 * | 1/1994 | (WO) . |
| WO 96/26280 | 8/1996 | (WO) . |

OTHER PUBLICATIONS

Ashkenas et al., "Proteolysis and the Biochemistry of Life–or–death Decisions", *J. Exp. Med.*, 183:1947–51 (1996).
Casciola–Rosen et al., "Apopain/CPP32 Cleaves Proteins that are Essential for Cellular Repair: A Fundamental Principle of Apoptopic Death," *J. Exp. Med.*, 183:1957–1964 (1996).
Chow et al., "Involvement of Multiple Proteases During Fas–mediated Apoptosis in T Lymphocytes," *FEBS Letters*, 364:134–138 (1995).
Duan et al., "ICE–LAP3, a Novel Mammalian Homolog of the *Caenorhabditis elegans* Cell Death Protein CED–3, Is Activated During Fas– and Tumor Necrosis Factor–induced Apoptosis", *J. Biol. Chem.*, 271:35013–35 (1996).
Enari et al., "Sequential Activation of ICE–like and CPP32–like Proteases During Fas–mediated Apoptosis", *Nature*, 380:723–26 (1996).
Faucheu et al., "A Novel Human Protease Similar to the Interleukin 1β Converting Enzyme Induced Apoptosis in Transfected Cells", *EMBO J.*, 14:1914–22 (1995).
Fernandes–Alnemri et al., "CPP32, a Novel human Apoptotic Protein with Homology to *Caenorhabditis elegans* Cell Death Protein CED–3 and Mammalian Interleukin 1β–Converting Enzyme", *J. Biol. Chem.*, 269:30761–64 (1994).
Fernandes–Alnemri et al., "Mch–2, a New Member of the Apoptotic CED–3/ICE Cysteine Protease Gene Family", *Cancer Res.*, 55:2737–42 (1995).
Fernandes–Alnemri, "Mch–3, a Novel Human Apoptotic Cysteine Protease Highly Related to CPP32", *Cancer Res.*, 55:6045–52 (1995).
Gluck et al., "The Selective Uptake of Benzoporphyrin Derivative Mono–acid Ring A Results in Differential Cell Kill of Multiple Myeloma Cells in vitro", *Photochem. Photobiol.*, 63:846–53 (1996).
Gomer et al., "Molecular, Cellular, and Tissue Response Following Photodynamic Therapy", *Las. Surg. Med.*, 8:450–63 (1988).
Jamieson et al., "Efficacy of Benzoporphyrin Derivative, a Photosensitizer, in Selective Destruction of Leukemia Cells Using a Murine Tumor Model", *Exp. Haematol.*, 21:629–34 (1993).
Kamens et al., "Identification and Characterization of ICH–2, a Novel Member of the Interleukin 1β–Converting Enzyme Family of Cysteine Proteases", *J. Biol. Chem.*, 270:15250–56 (1995).
Kaufmann et al., "Specific Proteolytic Cleavage of Poly–(ADP–ribosyl) Polymerase: An Early Marker of Chemotherapy–induced Apoptosis", *Cancer Res.*, 53:3976–85 (1993).
Kerr et al., "Apoptosis: A Basic Biological Phenomenon with Wide–ranging Implications in Tissue Kinetics," *Br. J. Cancer* 26:239–245 (1972).
Luo et al., "Rapid Initiation of a Apoptosis by Photodynamic Therapy," *Photochem. Photobiol.* 63:528–534 (1996).
Kumar et al., "Induction of Apoptosis by the Mouse Nedd2 Gene, Which Encodes a Protein Similar to the Product of the *Caenorhabditis elegans* Cell Death Gene ced–3 and the Mammalian IL–1–Converting Enzyme", *Genes Dev.*, 8:1613–26 (1994).

(List continued on next page.)

Primary Examiner—Sandra E. Saucier
(74) Attorney, Agent, or Firm—Morrison & Foerster, LLP (57) ABSTRACT

A composition and method for inhibiting apoptosis, or decreasing the rate or extent of apoptosis, in target cells. The method comprises the step of the step of contacting the target cells with an apoptosis-regulating amount of at least one cysteine or serine protease inhibitor that:

a. inhibits the conversion of the pro-enzyme form of CPP32 to its enzymatically-active form;
b. blocks the proteolytic action of activated CPP32 against its cellular substrates; or
c. both.

The method is particularly applicable to ameliorating the side effects of, or enhancing the selectivity, of photodynamic therapy.

7 Claims, 8 Drawing Sheets

OTHER PUBLICATIONS

Lazebnik et al., "Cleavage of Poly(ADP–ribose) Polymerase by a Proteinase with Properties Like ICE", *Nature* 371:346–47 (1994).

Lazebnik et al., "Studies of the Lamin Proteinase Reveal Multiple Parallel Biochemical Pathways During Apoptotic Execution", *Proc. Natl. Acad. Sci.*, 92:9042–46 (1995).

Lippke et al., "Identification and Characterization of CPP32/Mch–2 Homolog 1, a Novel Cysteine Protease Similar to CPP32", *J. Biol. Chem.* 271:1825–28 (1996).

Martin et al., "Protease Activation During Apoptosis: Death by a Thousand Cuts?", *Cell*, 82:349–352 (1995).

Munday, et al., "Molecular Cloning and Proapoptotic Activity of ICE rel–II and ICE rel III, Members of the ICE/CED–3 Family of Cystein Proteases", *J. Biol. Chem.*, 270:15870–76 (1995).

Muzio et al., "FLICE, a Novel FADD–Homologous ICE/CED–3–like Protease, is Recruited to the CD95 (Fas/APO–1) Death–inducing Signaling Complex," *Cell*, 85:817–827 (1996).

Nicholson et al., "Identification and Inhibition of the ICE/CED–3 Protease Necessary for Mammalian Apoptosis," *Nature*, 376:37–43 (1995).

Agarwal et al., "Photodynamic Therapy Induces Rapid Cell Death of Apoptosis in L5178 Mouse Lymphoma Cells," *Cancer Research* 51:5993–5996 (1991).

Salvensen et al., "Yama/CPP32β, A Mammalian Homolog of CED–3, is a CrmA–Inhibitable Protease that Cleaves the Death Substrate Poly(ADP–ribose) Polymerase," *Cell*, 81:801–809 (1995).

Schlegel e al., "CPP32/Apopain is a Key Interleukin 1β Converting Enzyme–like Protease Involved in Fas–mediated Apoptosis," *J. Biol. Chem.*, 271:1841–1844 (1996).

Takahashi et al., "Cleavage of Lamin A by Mch2α But Not CPP32: Multiple Interleukin 1β–converting Enzyme–related Proteases with Distinct Substrate Recognition Properties Are Active in Apoptosis", *Proc. Natl. Acad. Sci.*, 93:8395–8400 (1996).

Wang et al., "Ich–1, an ICE/ced–3–related Gene, Encodes Both Positive and Negative Regulators of Programmed Cell Death", *Cell.*, 78:739–50 (1994).

Yoon et al., "Poly (ADP–ribosyl)ation of Histone H1 Correlates with Internucleosomal DNA Fragmentation During Apoptosis," *J. Biol. Chem.*, 271:9129–9134 (1996).

Berg, K., et al., "The influence of the cysteine protease inhibitor L–trans–epoxysuccinyl–leucyl amido(4–guanidio)butane (E64) on photobiological effects of tetra(4–sulfonatophenyl)porphine," *Cancer Letters* (1995) 88:227–236.

Virgin, I., et al., "Light–induced D1 protein degradation is catalyzed by a serine–type protease," *FEBS Letters* (1991) 287(1,2):125–128.

Han, Z., et al., "DNA–dependent Protein Kinase Is a Target for a CPP32–like Apoptotic Protease," *The Journal of Biological Chemistry* (1996) 271(40):25035–25040.

Lotem, J., et al., "Differential suppression by protease inhibitors and cytokines of apoptosis induced by wild–type p53 and cytotoxic agents," *Proc. Natl Acad Sci USA* (1996) 93:12507–12512.

Shimizu, T., et al., "Camptothecin–induced apoptosis in p53–null human leukemia HL60 cells and their isolated nuclei: effects of the protease inhibitors Z–VAD–fmk and dichloroisocoumarin suggest an involvement of both caspases and serine proteases," *Leukemia* (1997) 11:1238–1244.

Sekine, C., et al., "Fas–Mediated Stimulation Induces IL–8 Secretion by Rheumatoid Arthritis Synoviocytes Independently of CPP32–Mediated Apoptosis," *Biochemical and Biophsical Research Communications* (1996) 228:14–20.

Anderson, T.L., et al., "Intracellular Signaling Pathways Involved in the Induction of Apoptosis in Immature Thymic T Lymphocytes," *Journal of Immunology* (1996) 156:4083–4091.

Bourinbaiar, A.S., et al., "Effect of Serine Protease Inhibitor, N–α–Tosyl–L–lysyl–Chloromethyl Ketone (TLCK), on Cell–Mediated and Cell–Free HIV–1 Spread," *Cellular Immunology* (1994) 155(1):230–236.

Kessel, D., et al., "The Role of Sub–Cellular Localization on PDT–Initiated Apoptosis," *Photochemistry Photobiology* (1996) 63:79S–80S in Abstracts of the $24^{th}$ Annual Meeting of the American Society for Photobiology.

Lu et al., "Calpain inhibitors and serine protease inhibitors can produce apoptosis in HL–60 cells", Arch. Biochem. Biophys. 334 (1): 175–181 (1996).*

Weis et al., "Cellular events in Fas/APO–1–mediated apoptosis in JURKAT T lymphocytes", Exp. Cell Res. 219 (2): 699–708 (1995).*

Dolle et al., "P1 Aspartate–Based Peptide alpha—((2, 6–dichlorobenzoyl)oxy)methyl Ketones as Potent Time–Dependent Inhibitors of Interleukin–1–beta–Converting Enzime", J. Med. Chem. 37 (5): 563–4 (1994).*

Little et al., "Inhibition of programmed cell death by cyclosporin", Comp. Biochem. Physiol., C: Comp. Pharmacol. Toxicol. 103C (3): 463–7 (1992).*

* cited by examiner

BPD + light + Z-Asp-DCB

FIG. 2E

BPD + light + TLCK

METHOD FOR INHIBITING APOPTOSIS INDUCED BY PHOTODYNAMIC THERAPY USING A CYSTEINE OR SERINE PROTEASE INHIBITOR

TECHNICAL FIELD

This invention relates generally to the field of medicine and pharmacotherapeutics, particularly with the proteolytic events leading to the rapid onset of apoptotic cell death. More specifically, the invention is a composition and method for inhibiting or decreasing the extent or rate of apoptosis in a subject, particularly in association with standard photodynamic therapy protocols, which involve administering a photosensitive agent and subsequently irradiating the subject with light of a wavelength that is absorbed by the photosensitive agent.

BACKGROUND ART

Photodynamic therapy ("PDT") is an approved cancer treatment that can be used for many purposes, such as the treatment of solid tumors; the impairment of blood-borne targets such as leukemic cells, immunoreactive cells, and unwanted microorganisms; the prevention of restenosis; the treatment of ocular neovascular disorders such as macular degeneration; and the removal of atherosclerotic plaque. PDT involves the topical or systemic application of a light-absorbing photosensitive agent, usually a porphyrin derivative, which accumulates selectively in target tissues. A particularly potent photosensitizer is benzoporphyrin derivative mono-acid ring A ("BPD-MA" or "verteporfin"), which is a second generation chlorin-type photosensitizer exhibiting distinct advances over its hematoporphyrin forerunners in terms of effectiveness at lower concentrations and ability to absorb longer, more penetrating wavelengths of light.

Upon irradiation with visible light of an activating wavelength, reactive oxygen species are produced in cells containing the photosensitizer, which promotes cell death. Evidence has been developed indicating that PDT using a photosensitizer may cause cells to die via an apoptotic pathway. Kessel et al., "Rapid Initiation of Apoptosis by Photodynamic Therapy", *Photochem. Photobiol.*, 63:528–34 (1996); Oleinik et al., "Photodynamic Therapy Induces Rapid Cell Death of Apoptosis in L5178 Mouse Lymphoma Cells", *Cancer Res.*, 51:5993–96 (1991).

Apoptosis is the term used to describe a type of cellular death that occurs in many tissues as a normal physiological process. Apoptosis is a morphologically distinct form of cell death that plays an important role during normal development, differentiation, and homeostasis or turnover of tissues. Also called "programmed cell death," this form of cellular demise involves the activation in cells of a built-in genetic program for cell suicide by which cells essentially autodigest.

The goal of apoptosis is to attain an orderly disintegration of cells into structures suitable for phagocytosis. Morphologically, apoptosis is begun by loss of contact with neighboring cells and smoothening of the cell surface (vesicle formation on the cell surface and membrane "blebbing"). It is further characterized by the concentration of the cytoplasm, endonuclease activity-associated chromatin condensation and pyknosis, and segmentation of the nucleus. The orderly disintegration of cells also includes the degradation of genomic DNA into nucleosomal fragments and cellular fission to form apoptotic bodies. The nucleosome units of the resulting DNA fragments are about 180–200 bases in size. The final fragments of apoptotic body cells are phagocytosed by neighboring cells. The remnants of these dead cells are then cleared almost without a trace by neighboring phagocytic cells, without resulting in inflammation or scarring.

Apoptosis thus stands in marked contrast to necrotic cell death caused, for example by oxygen-deprivation in myocardial infarction or stroke, where cells lose their energy supplies, rupture and spill their contents into the extracellular milieu. Morphologically, necrosis is characterized by marked swelling of mitochondria, swelling of cytoplasm and nuclear alteration, followed by cell destruction and autolysis. It occurs passively or incidentally. Tissue necrosis is generally caused by physical trauma to cells or a chemical poison.

The concept that apoptosis is a finely regulated process is now well established. Kerr et al., "Apoptosis: A Basic Biological Phenomenon with Wide-ranging Implications in Tissue Kinetics", *Br. J. Cancer*, 26:239–45 (1972). However, the precise molecular mechanism remains as yet uncharacterized.

Apoptosis is thus known to be involved in developmental and tissue specific processes that require the removal of cell populations. In addition to the normal physiological process where cells are turned over within the body, apoptosis can be induced to occur by cellular, hormonal or other stimuli to remove unwanted cells from the body. For example, apoptosis is also known to be involved in the immunological process of cell selection. Specifically, the killing of tumor cells and virus-infected cells by the immune system's cytolytic T-cells occurs via apoptosis following target recognition. Further, apoptosis accounts for cell death in a wide variety of clinically important areas. For example, essentially all chemotherapeutic drugs currently used in the treatment of cancer, as well as x-irradiation in may cases, ultimately kill malignant cells by activating intracellular pathways leading to apoptosis.

Dysregulation of apoptosis, however, may be involved in the pathogenesis of a number of disease states and pathological conditions, such as cancer, acquired immunodeficiency syndrome (AIDS), and neurodegenerative disorders. Specifically, during spontaneous tumor regression, tumor cell death has been shown to follow an apoptotic pathway. During HIV infection, virally induced T-cell death has been shown to follow an apoptotic pathway. And the death of neurons that occurs in diseases such as Alzheimer's dementia and Parkinson's disease shows many hallmarks of apoptosis.

Control of apoptosis has been shown to be useful with respect to specific cells having crucial relevance to developmental biology. Additionally, it would be useful to control apoptosis with respect to treatments involving viral and bacterial pathogens. Cancer chemotherapy could also be enhanced by controlling apoptotic pathways. Efforts have been made using conventional chemotherapy to treat many of the disease states that result in inappropriate apoptotic cell death, but have so far yielded only minor progress toward effective treatment.

The chemical induction of apoptosis is target cell dependent. Glucocorticoids, such as dexamethasone, have been shown to induce apoptosis in thymocytes. Cycloheximide, a known inhibitor of protein synthesis, and actinomycin D, a known inhibitor of mRNA transcription, have also been shown to be powerful inducers of apoptosis in many cell lines. Other inducers of apoptosis include UV irradiation, captothecin, aphidocholin, cisplatin, vincristine, and phorbol myristate acetate plus ionomycin, glucocorticoids, atrophy of hormone-dependent tissues, NK cell, killer cells, tumor necrosis factor (TNF), lymphotoxin (LT), and other cytokines.

The inhibition of apoptosis is also target cell dependent. In addition to being classified as apoptosis inducers, actinomycin D and cycloheximide have also been classified as powerful inhibitors of apoptosis in many cell lines. Other known apoptosis inhibitors include various endonuclease inhibitors, e.g., $Zn^{2+}$ and aurintricarboxylic acid.

Inhibition of apoptotic deletion of autoreactive T-cell clones may be achieved by treatment with immunosuppressant cyclosporin A. Other special inhibitors of apoptosis include various steroids and interleukins. The latter stage of apoptosis, i.e., the induction of fission events leading to the formation of apoptosis bodies, may be inhibited by the use of microfilament-disrupting agents, such as cytochalasin B and staurosporin. Agents that inhibit the expression of the oncogene cMyc or that cause the over-expression of the proto-oncogene bcl-2 can inhibit the induction of apoptosis. Calcium ion ($Ca^{+2}$) chelating agents; hematopoietic system cytokines, such as IL-3, granulocyte macrophage colony stimulating factor and granulocyte colony stimulating factor; IL-2; and the bcl-2 gene product have all been reported as being capable of repressing apoptosis.

Other apoptosis inhibitors include the carbostyril derivatives of Nakai et al., U.S. Pat. No. 5,464,833 issued Nov. 7, 1995; the unstable dynemicin-like enediyne compounds of Nicolaou, U.S. Pat. No. 5,500,432 issued Mar. 19, 1996; methods of decreasing the activity of the Bcl gene as described by Reed, U.S. Pat. No. 5,550,019 issued Aug. 17, 1996; and compositions containing phytogenic apoptosis inhibitors ("PAls") isolated from plants by Bathurst et al., U.S. Pat. No. 5,567,425 issued Oct. 22, 1996.

In the past few years, it has been shown that the proteolytic cleavage of key cellular substrates represents an important part of the biochemical events underlying apoptosis. Casciola-Rosen et al., "Apopain/CPP32 Cleaves Proteins That Are Essential for Cellular Repair: A Fundamental Principle of Apoptotic Death", *J. Exp. Med.,* 183:1957–64 (1996).

In the past, efforts to identify the cellular components involved in the apoptotic pathway have focused on identifying the signaling molecules and endonucleases capable of cleaving DNA at internucleosomal sites. However, recently, the emphasis has shifted toward examining the role of specific proteases in this process, in particular, the members of the interleukin 1β-converting enzyme ("ICE") family of cysteine proteases. Martin et al., "Protease Activation During Apoptosis: Death by a Thousand Cuts?", *Cell.,* 82:349–52 (1995).

One of the best described pro-apoptotic genes, CED-3, encodes a protein that is highly homologous to the mammalian ICE. Nicholson et al., "Identification and Inhibition of the ICE/CED-3 Protease Necessary for Mammalian Apoptosis", *Nature,* 376:37–43 (1995). ICE was the first-identified member of a class of cysteine proteases with nearly absolute specificity for aspartic acid residues. Nicholson et al., supra, and Martin et al., supra. The involvement of ICE proteases in both ultraviolet light (UV) and Fas-mediated killing has been well-documented. Casciola-Rosen et al., supra; Muzio et al., "FLICE, a Novel FADD-Homologous ICE/CED-3-like Protease, Is Recruited to the CD95 (Fas/APO-1) Death-inducing Signaling Complex", *Cell,* 85:817–27 (1996); Yoon et al., "Poly (ADP-ribosyl) ation of Histone HI Correlates with Internucleosomal DNA Fragmentation During Apoptosis", *J. Biol. Chem.,* 271:9129–34 (1996); Chow et al., "Involvement of Multiple Proteases During Fas-mediated Apoptosis in T Lymphocytes", *FEBS Lett.,* 364:134–38 (1995); and Schlegel et al., "CPP32/Apopain is a Key Interleukin 1β Converting Enzyme-like Protease Involved in Fas-mediated Apoptosis", *J. Biol. Chem.,* 271:1841–44 (1996). A number of different homologs in the ICE family have been characterized, as follows:

| Homolog | Reference |
|---|---|
| Yama/CPP32/Apopain | Nicholson et al., supra,; Fernandes-Alnemri et al., "CPP32, A Novel Human Apoptotic Protein with Homology to *Caenorhabditis elegans* Cell Death Protein CED-3 and Mammalian Interleukin 1β-Converting Enzyme", J. Biol. Chem., 269: 269-30761-64 (1994); and Salvesen et al., "Yama/CPP32β, a Mammalian Homolog of CED-3, Is a CrmA-Inhibitable Protease that Cleaves the Death Substrate Poly(ADP-ribose) Polymerase", Cell., 81: 801-809 (1995). |
| Nedd-2/ICH-1 | Kumar et al., "Induction of Apoptosis by the Mouse Nedd2 Gene, Which Encodes a Protein Similar to the Product of the *Caenorhabditis elegans* Cell Death Gene ced-3 and the Mammalian IL-1-Converting Enzyme", Genes Dev., 8: 1613-26 (1994); and Wang et al., "Ich-1, an ICE/ced-3-related Gene, Encodes Both Positive and Negative Regulators of Programmed Cell Death", Cell., 78: 739-50 (1994). |
| Tx/ICH-2/ICE rel-II | Gaucheu et al., "A Novel Human Protease Similar to the Interleukin 1β Converting Enzyme Induces Apoptosis in Transfected Cells", EMBO J., 14: 1914-22 (1995); Kamens et al., "Identification and Characterization of ICH-2, a Novel Member of the Interleukin 1β-Converting Enzyme Family of Cysteine Proteases", J. Biol. Chem., 270: 15250-56 (1995); and Munday, et al., "Molecular Cloning and Proapoptotic Activity of ICE rel-II and ICE rel III, Members of the ICE/CED-3 Family of Cysteine Proteases", J. Biol. Chem., 270: 15870-76 (1995). |
| ICE rel III | Munday et al., supra. |
| Mch-2 | Fernandes-Alnemri et al., "Mch-2, a New Member of the Apoptotic CED-3/ICE Cysteine Protease Gene Family", Cancer Res., 55: 2737-42 (1995). |
| ICE-LAP3/Mch-3/CMH-1 | Duan et al., "ICE-LAP3, a Novel Mammalian Homolog of the *Caenorhabditis elegans* Cell Death Protein CED-3, Is Activated During Fas- and Tumor Necrosis Factor-induced Apoptosis", J. Biol. Chem., 271: 35013-35 (1996); Fernandes-Alnemri, "Mch-3, a Novel Human Apoptotic Cysteine Protease Highly Related to CPP32", Cancer Res., 55: 6045-52 (1995); and Lippke et al., "Identification and Characterization of CPP32/Mch-2 Homolog 1, a Novel Cysteine Protease Similar to CPP32", J. Biol. Chem. 271: 1825-28 (1996). |
| ICE LAP6 | Muzio et al., supra. |

The ectopic expression of these ICE homologs has been shown to cause apoptosis in a variety of cell types. However, while cysteine proteases of the ICE/CED-3 family have been shown to play an important role in apoptosis induced by various deleterious and physiological stimuli, only CPP32

("Caspase-3/YAMA/apopain"; see *Cell*, 87:171 (1996)) and ICE-LAP3 have been shown to be proteolytically activated by conventional apoptotic stimuli. Muzio et al., supra.

The ICE homolog, CPP32, is a cysteine protease that is proteolytically activated by a variety of apoptotic stimuli. Muzio et al., supra. During UV light and Fas-mediated apoptosis, CPP32 is proteolytically cleaved from its precursor 32 kD (p32) to form the active enzyme composed of 17 kD (p17) and 12 kD (p12) subunits. Casciola-Rosen et al., "Apopain/CPP32 Cleaves Proteins That Are Essential for Cellular Repair: A Fundamental Principle of Apoptotic Death", *J. Exp. Med.*, 183:1957–64 (1996); Schlegel et al., "CPP32/Apopain is a Key Interleukin 1β Converting Enzyme-like Protease Involved in Fas-mediated Apoptosis", *J. Biol. Chem.*, 271:1841–44 (1996).

Many of the known proteolytic targets of ICE proteases are proteins associated with the cell nucleus, including lamins (major constituents of the nuclear envelope), globular actin, the nuclear mitotic apparatus protein NuMA, and the U1-70 kD protein (a component of the RNA splicing machinery). Proteolytic targets of ICE proteases also include other enzymes such as poly(ADP-ribose) polymerase (PARP) and the catalytic subunit of the DNA-dependent protein kinase (DNA-PKcs). Askansas et al., "Proteolysis and the Biochemistry of Life-or-death Decisions", *J. Exp. Med.*, 183:1947–51 (1996).

Even though the lamin protease is distinct from the CPP32 protease, cleavage of lamins, in particular, appears to be required for packaging condensed chromatin into apoptotic bodies. Takahashi et al., "Cleavage of Lamin A by Mch2α But Not CPP32: Multiple Interleukin 1β-converting Enzyme-related Proteases with Distinct Substrate Recognition Properties Are Active in Apoptosis", *Proc. Natl. Acad. Sci.*, 93:8395–8400 (1996); Lazebnik et al., "Studies of the Lamin Proteinase Reveal Multiple Parallel Biochemical Pathways During Apoptotic Execution", *Proc. Natl. Acad. Sci.*, 92:9042–46 (1995).

PARP is an enzyme that appears to serve in the surveillance and enzymatic repair of DNA damage caused by environmental stress. Nicholson et al., "Identification and Inhibition of the ICE/CED-3 Protease Necessary for Mammalian Apoptosis", *Nature*, 376:37–43 (1995); Kaufmann et al., "Specific Proteolytic Cleavage of Poly(ADP-ribosyl) Polymerase: An Early Marker of Chemotherapy-induced Apoptosis", *Cancer Res.*, 53:3976–85 (1993); Lazebnik et al., "Cleavage of Poly(ADP-ribose) Polymerase by a Proteinase with Properties Like ICE", *Nature* 371:346–47 (1994). Furthermore, the $Ca^{++}/Mg^{++}$-dependent endonuclease that is involved in the internucleosomal cleavage of DNA within apoptotic cells is negatively regulated by poly(ADP-ribos)ylation. Nicholson et al., supra. It has been postulated that loss of normal PARP function may render this nuclease highly active in dying cells. Id.

It has also been demonstrated that CPP32/Yama/Apopain is the protease responsible for the cleavage of PARP. Id.; Fernandes-Alnemri et al., "CPP32, a Novel human Apoptotic Protein with Homology to *Caenorhabditis elegans* Cell Death Protein CED-3 and Mammalian Interleukin 1β-Converting Enzyme", *J. Biol. Chem.*, 269:30761–64 (1994); and Salvesen et al., "Yama/CPP32β, a Mammalian Homolog of CED-3, Is a CrmA-inhibitable Protease that Cleaves the Death Substrate Poly(ADP-ribose) Polymerase", *Cell.*, 81:801–809 (1995). It has been shown that PARP (p116) is cleaved into 85 kD and 25 kD fragments under pro-apoptotic stimuli. Nicholson et al., supra; Salvesen et al., supra; Kaufmann et al., supra; Lazebnik et al., supra; and Enari et al., "Sequential Activation of ICE-like and CPP32-like Proteases During Fas-mediated Apoptosis", *Nature*, 380:723–26 (1996).

The basic response mechanism of apoptotic cell death that is induced by PDT has been studied, for example, by Jamieson et al., "Efficacy of Benzoporphyrin Derivative, a Photosensitizer, in Selective Destruction of Leukemia Cells Using a Murine Tumor Model", *Exp. Haematol.*, 21:629–34 (1993); Gomer et al., "Molecular, Cellular, and Tissue Response Following Photodynamic Therapy", *Las. Surg. Med.*, 8:450–63 (1988); Gluck et al., "The Selective Uptake of Benzoporphyrin Derivative Mono-acid Ring A Results in Differential Cell Kill of Multiple Myeloma Cells in vitro", *Photochem. Photobiol.*, 63:846–53 (1996); Kessel et al., "Rapid Initiation of Apoptosis by Photodynamic Therapy", *Photochem. Photobiol.* 63:528–34 (1996); and Oleinik et al., "Photodynamic Therapy Induces Rapid Cell Death by Apoptosis in L5178 Mouse Lymphoma Cells", *Cancer Res.*, 51:5993–96 (1991)). However, the pattern of protease activation in cells treated with PDT has not yet been addressed.

DISCLOSURE OF THE INVENTION

It has been discovered that PDT with a photosensitive agent such as BPD and visible light causes programmed cell death by evoking a cascade of proteolytic events that ultimately lead to cell death. Specifically, it has now been discovered that PDT, particularly when using benzoporphyrin derivative monoacid ring A ("BPD-MA" or "verteporfin") as a photosensitizer, induces the complete cleavage and subsequent activation of CPP32/Yama/Apopain. Moreover, it has been discovered that apoptosis can be inhibited, or the rate or extent of apoptosis can be reduced, in living cells, by contacting the living cells with an apoptosis-regulating amount of at least one cysteine or serine protease inhibitor that:

a. inhibits the conversion of the pro-enzyme form of CPP32 to its enzymatically-active form;

b. blocks the proteolytic action of activated CPP32 against its cellular substrates; or c. both.

The apoptosis inhibiting compositions and methods of the invention are of use as anticancer agents, anti-retrovirus agents, therapeutic agents for autoimmune diseases, therapeutic agents for thrombocytopenia, therapeutic agents for Alzheimer's disease, therapeutic agents for diseases of the liver, and cancer metastasis inhibitors, among others.

In another embodiment, the invention relates to a method of ameliorating the adverse affects of photodynamic therapy ("PDT"), or enhancing the selectivity of PDT, in a subject in need of PDT treatment, comprising the steps of:

a. administering to the subject an amount of photosensitive agent effective to selectively accumulate in target cells;

b. administering to the subject an apoptosis-regulating amount of at least one cysteine or serine protease inhibitor that:

(1) inhibits the conversion of the pro-enzyme form of CPP32 to its enzymatically-active form;

(2) blocks the proteolytic action of activated CPP32 against its cellular substrates.; or (3) both; and c. administering to the target cells a PDT-effective amount of light of a wavelength absorbed by said photosensitizing agent.

DETAILED DESCRIPTION OF THE INVENTION

"Living cells" in this application refers to either the normal or target cells within a subject. In some embodiments, the term "living cells" can refer to diseased cells exhibiting an inappropriately high rate or extent of apoptosis. Alternatively, "living cells" may also refer to the normal or non-diseased cells surrounding the undesirable cells that are being targeted, such as tumor cells or leukemic cells, in photodynamic therapy or some other form of chemotherapy.

It has been found that the exposure of living cells to certain apoptotic stimuli, such as photodynamic therapy, causes the proteolytic cleavage of certain enzymes, such as the nuclear enzymes CPP32/Yama/Apopain and poly(ADP-ribose) polymerase ("PARP"), and certain nuclear associated proteins, such as lamin $B_1$ and the catalytic subunit of DNA dependent protein kinase ("DNA $PK_{CS}$").

It has also been found that the protease activity of the thus-cleaved CPP32 can be inhibited with an ICE peptide inhibitor, such as Z-Asp-2,6-dichlorobenzyloxymethylketone ("Z-Asp-DCB"), which completely blocks apoptotic DNA fragmentation. The induction of apoptosis can also be blocked by other cysteine protease inhibitors, such as N-ethylmaleimide and iodoacetamide, and by serine protease inhibitors, such as 3,4-dichloroisocoumarin and N-tosyl-lysine chloromethyl ketone ("TLCK"). While not wishing to be bound by the theory set forth, it is believed that the Z-Asp-DCB may inhibit apoptosis by inhibiting the proteolytic activity of CPP32, while TLCK may suppresses apoptosis by blocking the proteolytic activation of CPP32. See FIG. 7. However, it does appear more clearly that the cysteine protease CPP32 plays an important role in apoptosis, particularly in PDT-induced apoptosis.

The apoptosis-inhibiting composition of the invention can comprise any cysteine or serine protease inhibitor that:
 a. inhibits the conversion of the pro-enzyme form of CPP32 to its enzymatically-active form;
 b. blocks the proteolytic action of activated CPP32 against its cellular substrates; or
 c. both.

Examples of useful cysteine protease inhibitors include those in the interleukin 1β-converting enzyme ("ICE") inhibitors, such as Z-Asp-2,6-dichlorobenzoyloxymethylketone ("Z-Asp-DCB"), Acetyl-Asp-Glu-Val-Asp-CHO ("AC-DEVD-CHL") and the like; N-ethylmaleimide; iodoacetamide; and the like. Examples of useful serine protease inhibitors include trypsin and chymotrypsin inhibitors, such as N-α-tosyl-L-arginine methyl ester ("TAME"), N-α-tosyl-L-lysyl-chloromethane ("TLCK"), and N-α-tosyl-L-phenylalanyl-chloromethane ("TPCK"); $α_1$-proteinase inhibitor (often called $α_1$-antitrypsin), which inhibits a broad spectrum of serine proteases; urokinase; soybean trypsin inhibitor; ovomucoid; 3,4-dichloroisocoumarin; and the like.

The many cellular substrates lysed by CPP32 include, for example, DNA-dependent protein kinase (DNA-$PK_{CS}$), poly(ADP-ribose) polymerase (PARP), steroid regulatory element-binding proteins, and the 70 kDa V1 ribonuclear protein.

To test the ability of a particular cysteine or serine protease inhibitor to
 a. inhibit the conversion of the pro-enzyme form of CPP32 to its enzymatically-active form.
 b. block the proteolytic action of activated CPP32 against its cellular substrates, or
 c. both,
thus inhibiting apoptosis, the following test can be performed, in accordance with the method described by Nicoletti et al., *J. Immunological Methods,* 139:271–79 (1991): CMK cells are suspended in RPMI-1640 medium supplemented with 10% fetal calf serum (FCS) at a concentration of $5×10^4$ cells/mL. The test compound is added to the cell suspension at a concentration of 30 mu g/mL. The mixture is incubated in the wells of a six-well microtiter plate at 37° C. for four days. As a control, the vehicle alone is added to a similar suspension, and the mixture is incubated in the same manner. After cultivation, the cells are recovered. About $1×10^6$ cells are transferred into a polyethylene tube and centrifuged at 200× g for five minutes to form a pellet.

The pellet obtained is re-suspended in 0.25 mL of buffer and 50 mu g/mL of propidium iodide (PI, Sigma, 100 mu g/mL in PBS) in 0.1% sodium citrate (Wako Pure Chemical)+0.1% Triton X-100 (Katayama Kagaku). Prior to flow cytometric analysis, the tube is allowed to stand in the dark at 4° C. overnight. The PI fluorescence of individual nuclei is determined by a Profile II (Coulter) flow cytometer. For this purpose, a 488 nm argon laser is used at 1 W. For focusing the red fluorescence of PI-stained DNA, a 560 nm dichromic mirror DM570 and a 600 nm band-pass filter (bandwidth 35 nm) are used. The residual cell fragments show extremely low DNA red fluorescent emissions, while intact apoptotic cells show a high SSC value, owing to the concentration of nuclear chromatin. The flow velocity ratio is set at about 200 nuclei/second, and each sample is analyzed for at least $10^4$ nuclei. Cell fragments with low intensities of fluorescence were excluded. The proportion of nuclei showing a content of not less than 2N is regarded as the share of intact apoptotic cells and is used as an indicator of apoptosis inhibition.

In the composition of the invention, an apoptosis-regulating amount of the compound of the invention is present. By "apoptosis-regulating amount" is meant an amount effective to decrease the level or extent of apoptosis by at least about 70% as measured by flow cytometry, preferably at least about 80% and, most preferably, by at least about 90%. The concentrations of the compound to be used in the composition and method of the invention can vary greatly, depending chiefly on cell type. However, typically, the concentration varies from about 20 to 200 μg/mL, preferably from about 40 to about 100 μg/mL.

The pharmaceutical composition of the invention may also comprise a pharmaceutically acceptable carrier, such as saline, buffered saline, 5% dextrose in water, borate-buffered saline containing trace metal, carboxymethyl cellulose, vegetable oil, DMSO, ethanol, and the like. Formulations may further include one or more excipients, preservatives, solubilizers, buffering agents, albumin to prevent protein loss on vial surfaces, lubricants, fillers, stabilizers, and the like. Methods of formulation are well-known in the art and are disclosed, for example, in *Remington's Pharmaceutical Sciences,* Mack Publishing Co., Easton, Pa. (Gennaro, ed. 1990), which is incorporated herein by reference.

Pharmaceutical compositions for use within the present invention can be in the form of sterile, non-pyrogenic liquid solutions or suspensions, e.g., for injections or eye drops, emulsions, granules, tablets, pills, coated capsules, suppositories, lyophilized powders, transdermal patches, or other forms known in the art. Such preparations are prepared using the conventional fillers, extenders, binding agents, moistening agents, disintegrating agents, surfactants, lubricants, and the like diluents or excipients.

For the manufacture of tablets, a wide variety of carriers known in this field can be used. Thus, useful carriers include, for example, vehicles or excipients such as lactose, sucrose, sodium chloride, glucose, urea, starch, calcium carbonate, kaolin, crystalline cellulose and silicic acid; binding agents such as water, ethanol, propanol, simple syrup, glucose solution, starch solution, gelatin solution, carboxymethylcellulose, shellac, methylcellulose, potassium phosphate and polyvinylpyrrolidone; disintegrating agents such as dry starch, sodium alginate, powdered agar, powdered laminaran, sodium hydrogen carbonate, calcium carbonate, polyoxyethylene sorbitan fatty acid esters, sodium lauryl sulfate, stearic acid monoglyceride, starch and lactose; disintegration inhibitors such as sucrose, stearin, cacao butter and hydrogenated oils; absorption promoters such as quaternary ammonium bases and sodium lauryl sulfate; wetting agents or humectants such as glycerol and starch; adsorbents such as starch, lactose, kaolin, bentonite and colloidal silica; and lubricants such as refined talc, stearic acid salts, powdered boric acid and polyethylene glycol. When appropriate, the tablets may further be provided with a conventional coating to give, for example, sugar-coated tablets, gelatin-coated tablets, enteric-coated tablets, film-coated tablets, or double-coated or multilayer tablets.

For the manufacture of pills, a wide variety of carriers well-known in the art can be used. Examples are vehicles or excipients such as glucose, lactose, starch, cacao butter, hardened vegetable oils, kaolin and talc; binding agents such as powdered gum arabic, powdered tragacanth gum, gelatin and ethanol; and disintegrating agents such as laminaran and agar.

For the manufacture of suppositories, a wide variety of carriers so far know can be used. As examples, there may be mentioned polyethylene glycol, cacao butter, higher alcohols, higher alcohol esters, gelatin and semi-synthetic glycerides.

In preparing fluids for injection, the solutions or suspensions are preferably sterilized and isotonic with blood. For preparing such dosage forms, all the diluents in conventional use in this field can be employed. Thus, for example, water, ethyl alcohol, propylene glycol, ethoxylated isostearyl alcohol, polyoxylated isostearyl alcohol and polyoxyethylene sorbitan fatty acid esters may be mentioned. In this case, the pharmaceutical preparations may contain sodium chloride, glucose or glycerol in an amount sufficient to give isotonic solutions. It is possible to add conventional solubilizing agents, buffers, soothing agents or local anesthetics, etc. Further, when appropriate, the pharmaceutical preparations may contain coloring materials, preservatives, perfumes, flavoring agents, sweetening agents and the like.

The proportion of the active ingredient compound in these pharmaceutical preparations of the invention is not critical, but may suitably be selected from a wide range. Generally, however, the proportion is preferably selected with the range of from about 1 to about 70% by weight.

The route of administration of these pharmaceutical preparations is not critical, but may be selected according to the dosage form, the patient's age, the severity of the disease to be treated and other factors. Thus, for instance, when they provided in the form of tablets, pills, solutions, suspensions, emulsions, granules or capsules, the preparations are typically administered orally. Injectable solutions are usually administered intravenously, either alone or in admixture with conventional fluids for parenteral infusion containing glucose, amino acids and the like.

Local administration may be by injection at the site of the living cells, by insertion or attachment of a solid carrier at the site, or by direct, topical application of a viscous liquid. Specifically, when necessary, solutions may be administered as is by the intramuscular, intradermal, subcutaneous or intraperitoneal route. Suppositories are administered rectally, and eye drops are instilled into the eye. The delivery of the compounds of the invention to living cells may be enhanced by the use of controlled-release compositions. Administration is preferably by topical application.

This invention provides a method of treating live cells, which includes, but is not limited to, intact animals such as humans and other mammals. The "mammals" also includes farm animals, such as cows, hogs and sheep, as well as pet or sport animals, such as horses, dogs and cats. While the dosage of the pharmaceutical compositions of the invention is dependent on the method of administration, the patient's age, severity of the disease, and the like, it is generally recommended to administer about 0.001 to 100 mg as the active ingredient per kilogram of body weight per day. The amount of the active ingredient to be contained in each dosage unit is typically about 0.01 to 1000 mg.

The apoptosis inhibiting compound and composition of the invention has, in addition to the apoptosis inhibiting ability, cell differentiation-inducing activity, cancer cell growth inhibitory activity, anticancer activity, anti-retrovirus activity, protection against shock death from endotoxin, cytokine production inhibitory activity, peripheral lymphocyte activation inhibitory activity and the like. Based on these activities, the apoptosis-inhibiting compound and composition of the invention can be used as, for example, an anticancer agent, a cancer metastasis-inhibitory agent, a therapeutic agent for thrombocytopenia, a therapeutic or prophylactic agent for Alzheimer's diseases and for liver diseases, an anti-retrovirus agent, a cytokine production inhibitory agent, and an immunosuppression agent.

The apoptosis inhibiting composition of the present invention, when administered as an anticancer composition, can be used in combination with one or more of other various anticancer agents known as cancer chemotherapeutic agents and/or radiation therapy. The active ingredient compound of the invention can thus markedly promote the effect of the other anticancer agent or agents combinedly used, to produce a synergistic effect. Therefore, even when the partner anticancer agent or agents are used in doses much smaller than the usual doses, a satisfactory anticancer effect can be obtained, and the adverse effects of the partner anticancer agent or agents can be minimized. As such chemotherapeutic agents, there may be used, for example, 5-fluorouracil, mitomycin C, futraful, endoxan and toyomycin.

When used in the treatment of thrombocytopenia, the apoptosis inhibiting composition of the invention can produce an apoptosis-suppressing action in patients with NIDS such as RAEB or RAEB-5. Administration of the composition of the invention can result in inhibition of blast cell multiplication, and proliferation of mature cells can then occur. The composition can further be expected to act on pro-megakaryocytes and megakaryocytes and promote their differentiation and maturation, thereby promoting thrombopoiesis. The use in the treatment of thrombocytopenia, the apoptosis inhibiting composition of the invention can be used in combination with one or more other known drugs such as thrombopoiesis-promoting agents to potentiate these partner drugs. This, in some instances, even when the partner drugs are used in fairly reduced doses, a satisfactory therapeutic effect can be produced and the adverse effects of these drugs can be thereby reduced.

The apoptosis-inhibiting composition of the present invention has an anti-retrovirus activity, and is useful as an anti-retrovirus agent for retrovirus-related diseases, such as HIV or HTLV-I-related diseases and C-type hepatitis.

Further, the apoptosis-inhibiting composition of the present invention has a peripheral lymphocyte activation inhibitory activity, as is exhibited, for example, by cyclosporin A. The compounds of the invention can be used effectively as an immunosuppression agent for inhibiting the rejection of an organ transplant and for autoimmune diseases, such as Behcet disease, sympathetic uveitis, psoriasis, aplastic anemia and the like.

In a particularly preferred embodiment, the method of the invention is used to ameliorate the adverse affects of photodynamic therapy ("PDT"), or to enhance the selectivity of PDT, in a subject in need of PDT treatment. In this embodiment, the method comprises the steps of:

a. administering to the subject an amount of photosensitive agent effective to selectively accumulate in target cells;
 b. administering to the subject an apoptosis-regulating amount of at least one cysteine or serine protease inhibitor that:
   (1) inhibits the conversion of the pro-enzyme form of CPP32 to its enzymatically-active form;
   (2) blocks the proteolytic action of activated CPP32 against its cellular substrates; or
   (3) both; and
 c. administering to the target cells a PDT-effective amount of light of a wavelength absorbed by said photosensitizing agent.

A "photosensitizing agent" is a chemical compound that homes to one or more types of selected target cells and, when exposed to light, absorbs light energy to result in the impairment or destruction of the target cells. Virtually any chemical compound that homes to a selected target and absorbs light may be used in this invention. Preferably, the chemical compound is nontoxic to the live cells with which it is brought into contact or is capable of being formulated in a nontoxic composition. Preferably, the chemical compound in its photodegraded form is also nontoxic. A comprehensive listing of photosensitive chemicals may be found in Kreimer-Birnbaum, *Sem. Hematol,* 26:157–73 (1989).

Photosensitive compounds include, but are not limited to, chlorins, bacteriochlorins, porphyrins, purpurins, merocyanines and pro-drugs such as δ-aminolevulinic acid, which can produce drugs such as protoporphyrin. Preferred are benzoporphyrin derivatives (BPDs) and porfimer sodium. Most preferred is the benzoporphyrin derivative monoacid ring A (BPD-MA).

The precise selection of an appropriate photosensitizer will be affected by such factors as the ability of the compound to localize within the cell, the ability of the compound to influence cell signaling events that link the formation of reactive oxygen species following PDT with the proteolytic events leading to apoptosis, and DNA fragmentation.

The photosensitive agent can be synthesized as a dimer, to absorb more light on a per mole basis. The photosensitizing agent also can be conjugated to specific lignads reactive with a target, such as receptor-specific ligands or immunoglobulins or immunospecific portions of immunoglobulins, permitting them to be concentrated in a desired target cell. This conjugation may permit lowering of the required dose level, since the material is more selectively targeted, and less is wasted in distribution into other tissues where destruction must be avoided.

When the live cells are contained within a live, intact animal, the photosensitizing agent is administered locally or systemically. The photosensitizing agent is administered orally or by injection, which may be intravenous, subcutaneous, intramuscular or intraperitoneal. The photosensitizing agent also can be administered enterally or topically via patches or implants.

The photosensitizing agent can be administered in a dry formulation, such as pills, capsules, suppositories or patches. The photosensitizing agent also may be administered in a liquid formulation, either alone with water, or with other pharmaceutically acceptable excipients, such as are disclosed *Remington's Pharmaceutical Sciences,* cited above. When liquid, the photosensitizer formulation can be a suspension or an emulsion. In particular, liposomal or lipophilic formulations are most desirable. If suspensions or emulsions are used, suitable excipients include water, saline, dextrose, glycerol, and the like. These photosensitizer compositions may contain minor amounts of nontoxic auxiliary substances, such as wetting or emulsifying agents, antioxidants, pH buffering agents, and the like.

The dose of the photosensitizing agent will vary with the target cell(s) sought and the weight and optimal blood level of the animal, when, as preferred the live cells are within an intact animal. Depending on the photosensitizing agent used, an equivalent optimal therapeutic level will have to be established. Preferably, the dose is calculated to obtain a blood level between about 0.01 and 100 $\mu$g/mL. Preferably, the dose will obtain a blood level between about 0.01 and 10 $\mu$g/mL. When the photosensitizing agent is BPD-MA, the blood level is preferably between about 0.01 and 4 $\mu$g/mL.

The photosensitizing agent is generally brought into contact with the live cells before they are subjected to the inhibitor compound or irradiation with light. The time between the administration of the photosensitive agent and the administration of inhibitor compound can vary greatly. However, a typical range of times would be from about 20 to about 40 minutes prior to light treatment, for example, about 30 minutes prior to light treatment.

"Radiation" as used herein includes all wavelengths. Preferably, the radiation wavelength is selected to match the wavelength(s) that excite the photosensitive compound. Even more preferably, the radiation wavelength matches the excitation wavelength of the photosensitive compound and has low absorption by the non-target cells and, if in vivo, by the rest of the intact animal, including blood proteins. For example, the preferred wavelength for BPD-MA is the range of from about 600 to 900 nm.

The radiation is further defined in this invention by its intensity, duration, and timing with respect to dosing with the photosensitive agent. The intensity must be sufficient for the radiation to reach the desired target cells. Both intensity and duration must be limited to avoid overtreating the surrounding normal cells. The intensity of radiation at the target cells is preferably between about 2 and 150 mW/cm². The duration of radiation exposure is preferably between about 0.25 minute and 24 hours. More preferably, the duration of radiation exposure is between about 0.25 minute and six hours. Most preferably, the duration of radiation exposure is between about 0.25 minute and two hours.

Timing with respect to dosing with the photosensitive agent is important, because 1) the administered photosensitive agent requires some time to home in on target cells and 2) the level of many photosensitive agents decreases rapidly with time.

EXAMPLES

Example 1

All drugs and chemicals, unless otherwise specified, were obtained from Sigma Chemical Company (St. Louis, Mo.). Photodynamic and inhibitor treatment of cells.

To identify possible mechanisms of cell death caused by PDT, a lethal combination of a benzoporphyrin derivative photosensitizer and light was given to cells. A human promyelocytic leukemia HL-60 cell line was obtained from the American Type Culture Collection (Rockville, Md.) and maintained in RPMI 1640 medium supplemented with 10% heat-inactivated fetal bovine serum (FBS), 4 mM L-glutamine, 1 mM sodium pyruvate, 1 mM Hepes, penicillin (100 U/mL), and streptomycin (100 µg/mL) purchased from Gibco BRL (Burlington, Ontario). Liposomally-formulated benzoporphyrin derivative monoacid ring A ("BPD-MA") was provided by QLT PhotoTherapeutics Inc. (Vancouver, British Columbia).

The HL-60 cells were incubated for 60 minutes at 37° C. with or without BPD (100 ng/mL) in RPMI and 2% FBS. Various broad range biochemical inhibitors were added to the cells prior to their exposure to light. Specifically, after 40 minutes of incubation with BPD, one of the following inhibitors was added to each experimental sample for an additional 20 minutes' incubation:

500 µM iodoacetamide,

500 µM N-ethylmaleimide,

Z-Asp-DCB (50 µg/mL),

Z-AAD-CMK (100 µg/mL), dichloroisocoumarin (40 µg/mL),

100 µM TLCK, 1 mM phenylmethylsulfonyl fluoride ("PMSF"), or aprotinin (50 µg/mL).

N-ethylmaleimide, iodoacetamide and 3,4-dichloroisocoumarin were obtained from Sigma Chemical Co. (St. Louis, Mo.). The ICE inhibitor III (Z-Asp-2,6-dichlorobenzoyloxymethylketone) was provided by Bachem (Torrance, Calif.). The negative control peptide Z-Ala-Ala-Asp-$CH_2Cl$ ("Z-AAD-CMK") was purchased from Calbiochem (Cambridge, Mass.).

Control samples were also prepared using a vehicle alone, such as dH20, methanol, or dimethyl sulfoxide (DMSO).

The incubated cells were then exposed to fluorescent red light having a wavelength of 620–700 nm at 5.6 mW/cm² to give a total light dose of 2 J/cm².

Flow cytometric detection of apoptosis

The resultant proportion of cells exhibiting DNA fragmentation was determined using a propidium iodide ("PI") fluorescence analysis procedure, which was used to detect changes in the status of cellular DNA, in accordance with a procedure set out by Telford et al., "Rapid Quantitation of Apoptosis in Pure and Heterogeneous Cell Populations Using Flow Cytometry", *J. Immunological Methods*, 172:1–16 (1994) or Darzynkieicz et al., "Features of Apoptotic Cells Measured by Flow Cytometry", *Cytometry*, 13:795–808 (1992).

Three hours following PDT, 1×10⁶ cells were washed twice with ice-cold PBS and then permeabilized and fixed in 80% ethanol at 4° C. for one hour. The cells were washed twice in ice-cold PBS and stained with PI (50 µg/mL) in PBS with simultaneous RNAse treatment (5 U/mL, DNase-free). The samples were analyzed by flow cytometry. The percentage of apoptotic cells was calculated using single parameter cytometry for PI fluorescence. Single parameter cytometry was deemed sufficient since the separation between the apoptotic population and cells within the $G_0/G_1$ region was considerable. Telford, supra. Cell fluorescence was analyzed with an Epics XL flow cytometer (Hialeah, Fla.).

Figure 1:
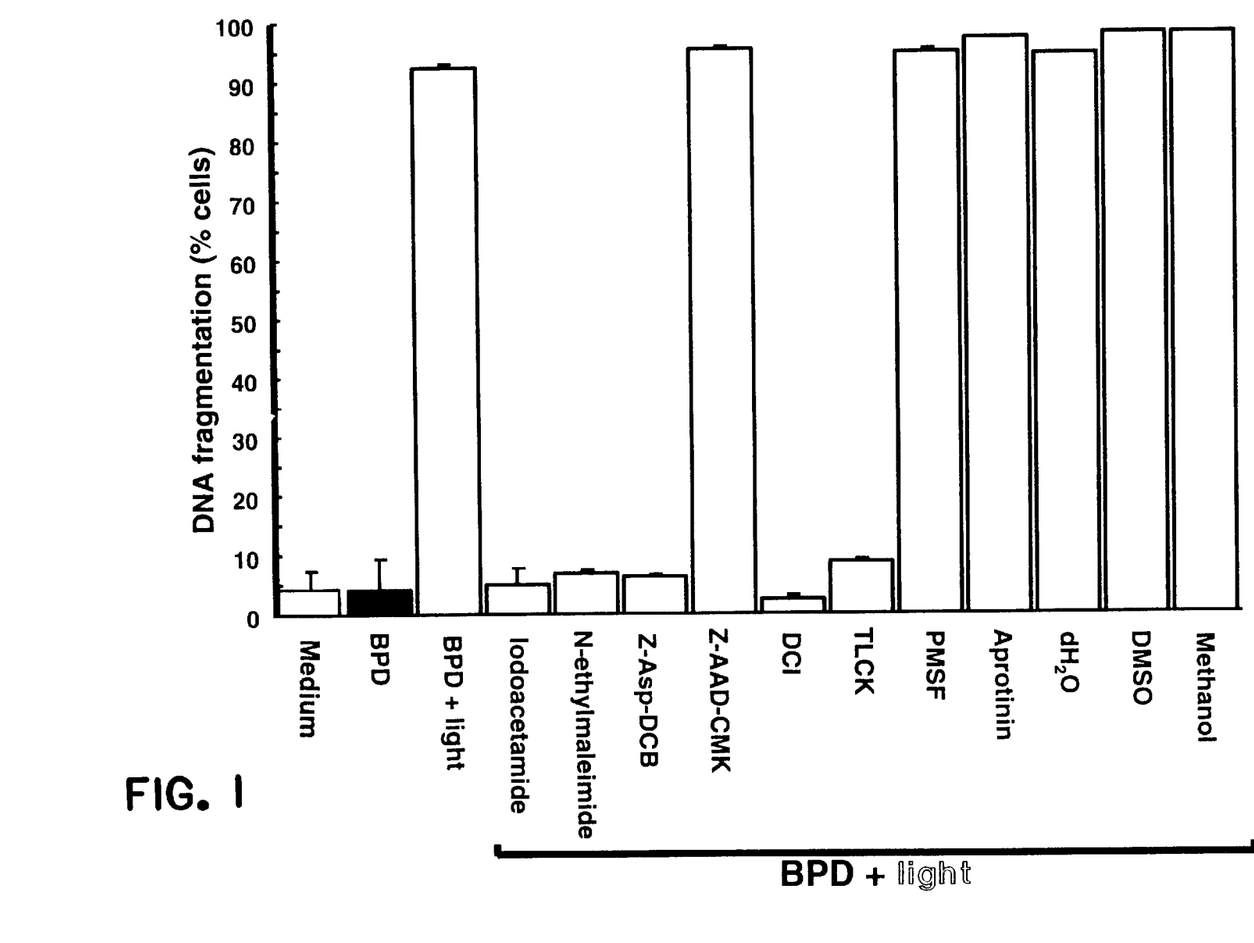
FIG. 1 shows the influence of various protease inhibitors on DNA fragmentation three hours after PDT.
Figure 2A:
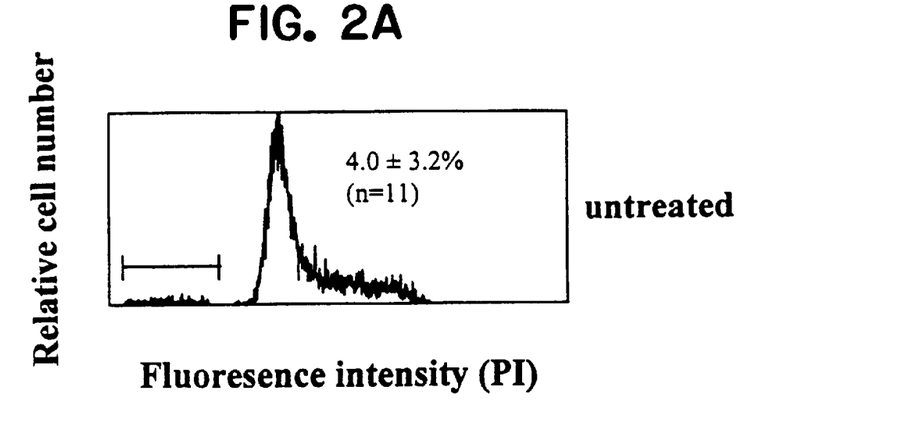
FIG. 2 shows DNA fragmentation in HL-60 cells treated with BPD and light.
Figure 2B:
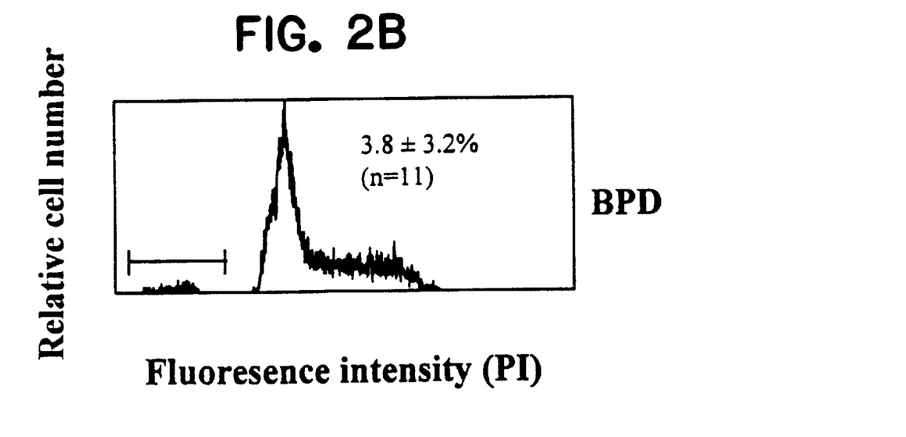
Figure 2C:
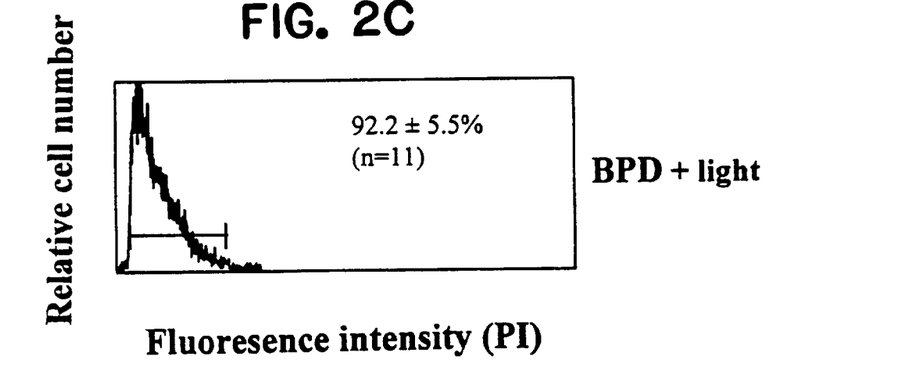
Figure 2D:
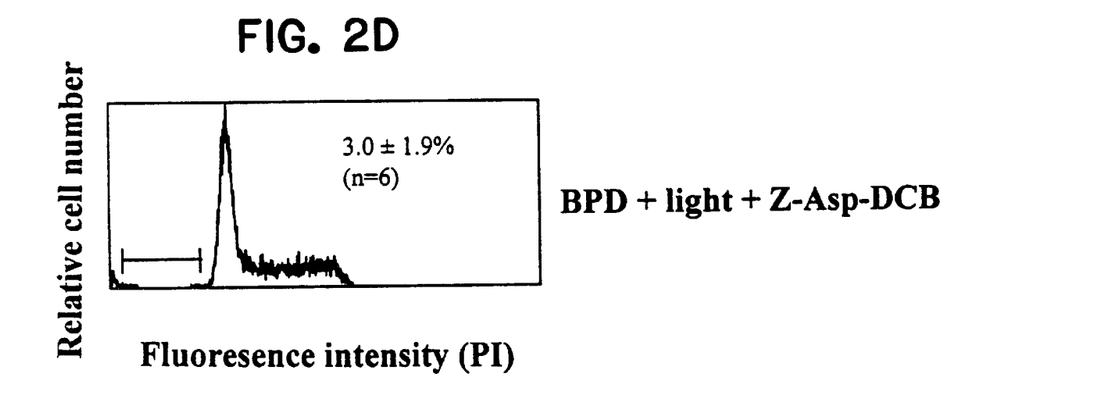
Figure 2E:
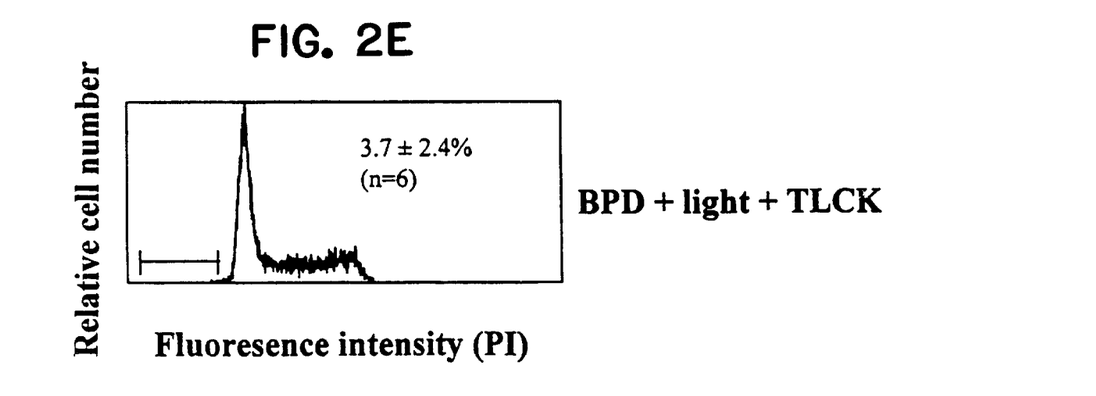

A high proportion of cells treated with BPD and light (complete PDT-treatment) exhibited DNA fragmentation (91.9±5.3%, n=11) within three hours of photosensitization, as compared with only 4.3±2.9% (n=11) for untreated cells (medium only) and 4.1±3.0% (n=11) for cells treated with BPD alone, as shown in FIG. 1.

The extent of DNA fragmentation was also observed for the samples treated with inhibitors (n=6) after three hours. As shown in FIG. 1, the cysteine protease inhibitors N-ethylmaleimide and iodoacetamide and the serine protease inhibitors 3,4-dichloroisocoumarin and TLCK were the only inhibitors that produced a protective effect as compared with the vehicle only samples (n=2), completely preventing any increase in DNA fragmentation induced by PDT.

To determine whether ICE proteases were involved, the membrane-soluble ICE inhibitor peptide Z-Asp-DCB was added to some of the samples prior to photosensitization. As a result, the PDT-induced DNA fragmentation was completely blocked, showing only background levels (6.4±1.7%; n=6), as shown in FIG. 2. At three hours following photosensitization, the cells were fixed with 80% ethanol, stained with PI, and analyzed by flow cytometry for DNA fragmentation. The percentage of apoptotic cells was calculated using single parameter flow cytometric analysis for PI fluorescence. The proportion of cells detected within the bar region of FIG. 2 represented cells exhibiting less than 2N DNA.

However, the other inhibitors and the vehicles not containing inhibitors had no effect on DNA fragmentation, as seen in FIG. 1. This was surprising because it has been shown that precursors of ICE and CPP32 can be processed by other enzymes, such as GraB and also by ICE itself, in Fas-mediated apoptosis of cytotoxic lymphocytes. Quan et al., "Proteolytic Activation of the Cell Death Protease Yama/CPP32 by Granzyme B", *Proc. Natl. Acad. Sci.*, 93:1972–76 (1996). Yet, the GraB inhibitor peptide (Shi et al., "Purification of Three Cytotoxic Lymphocyte Granule Serine Proteases that Induce Apoptosis Through Distinct Substrate and Target Cell Interactions", *J. Exp. Med.*, 176:1521–29 (1992)), Z-AAD-CMK, had no inhibitory effect on DNA fragmentation.

Example 2

To further explore proteolytic activity and the kinetics of proteolytic cleavage, HL60 cells were treated with PDT and lysed 0, 15, 30, 60 or 120 minutes later.

Preparation of cellular protein extracts

The cells were initially washed twice with ice-cold PBS. Cell pellets were then lysed in 1 mL of lysis buffer (1%

Nonidet P-40 detergent, 20 mM Tris, pH 8, 137 mM NaCl, 10% glycerol), supplemented with 1 mM PMSF, aprotinin (0.15 U/mL), and 1 mM sodium orthovanadate for 20 minutes on ice. Lysates were then centrifuged for 10 minutes at 15,800× g at 4° C. Protein concentrations of the cell extracts were determined by the Pierce BCA Protein Assay (Pierce, Rockford, Ill.).

Western immunoblotting

Cell lysates were separated by sodium dodecyl sulfate polyacrylamide gel electrophoresis (SDS-PAGE) and probed with anti-PARP or anti-CPP32 antibodies. Specifically, detergent-soluble proteins (30 µg) were separated by SDS-PAGE in 10.0% gels under reducing conditions, as described by Laemmli et al., "Cleavage of Structural Proteins During the Assembly of the Head of Bacteriophage T4", Nature, 227:680–85 (1970). The proteins were transferred to nitrocellulose membrane at 100 V for one hour. The nitrocellulose membranes were blocked for 30 minutes at room temperature with 5% skim milk in PBS. The blocked membranes were incubated for 45 minutes using the following antibody concentrations:

polyclonal goat-anti-PARP (1 µg/ml), monoclonal mouse-anti-lamin $B_1$ (2 µg/mL), polyclonal goat-anti-DNA-$PK_{CS}$ (1 µg/mL), and polyclonal goat-anti-CPP32 (1 µg/mL).

All antibodies were purchased from Santa Cruz Biotechnology Inc. (Santa Cruz, Calif.), except anti-lamin $B_1$, which was purchased from Calbiochem (Cambridge, Mass.).

The membranes were probed for primary antibodies for 30 minutes at room temperature with their respective secondary antibody at the following concentrations: anti goat-IgG-HRP (1:2000) or anti-mouse IgG-HRP (1:2000). Biotinylated molecular weight standards were probed with streptavidin-HRP (1:5000) conjugate (Amersham, Canada) in PBS-0.1% Tween 20 (PBS-T) for 30 minutes. The membrane was immediately rinsed twice in PBS-T, followed by three 15-minute washes with PBS-T. The proteins were detected using the enhanced chemiluminescence detection system (Amersham, Canada), and bands were visualized by autoradiography.

Figure 3A:
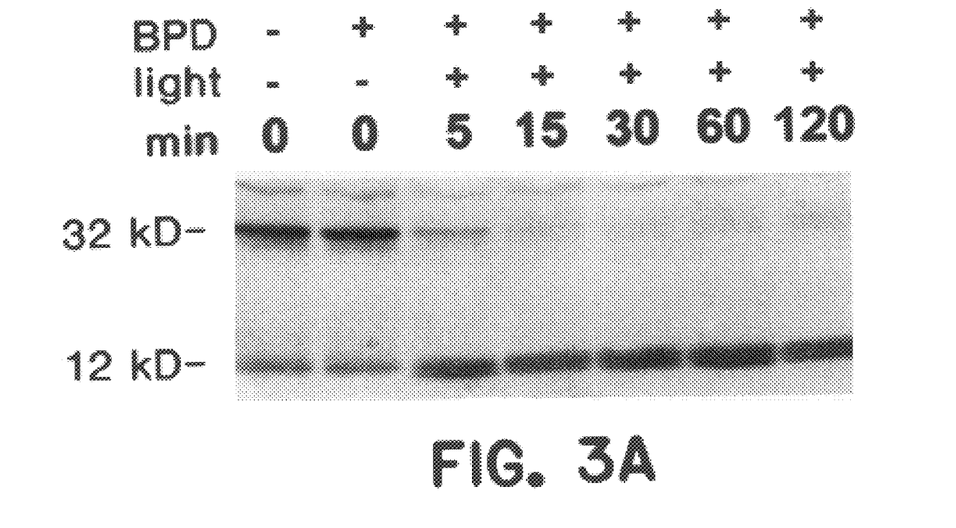
FIG. 3 shows the proteolytic cleavage of CPP32 and PARP, which precedes endonucleocytic DNA degradation in PDT-treated HL-60 cells.
Figure 3B:
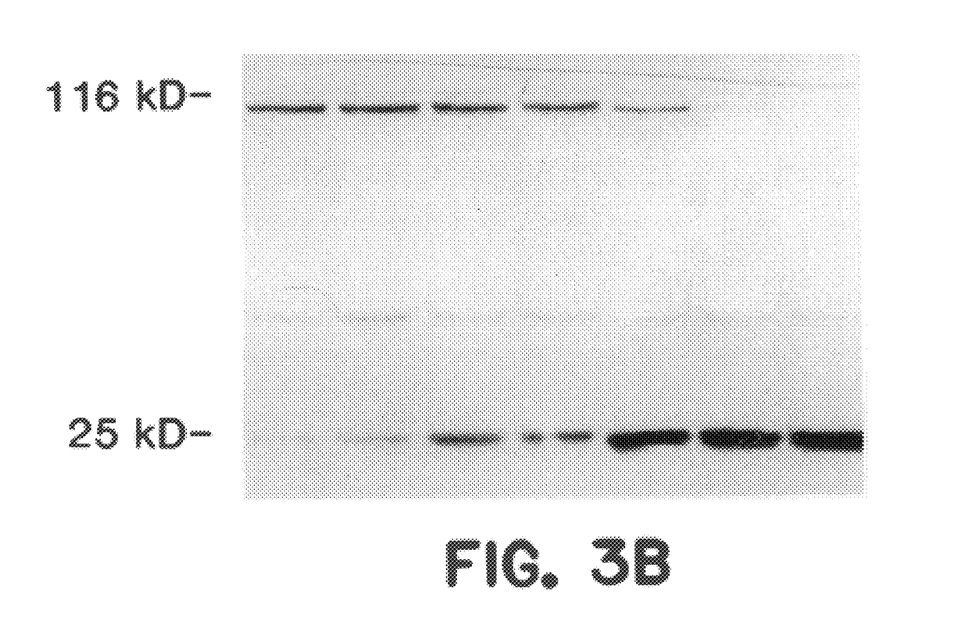

CPP32 was completely cleaved by 15 minutes, as shown in FIG. 3A, while PARP was fully cleaved by 60 minutes post-PDT, as shown in FIG. 3B. In FIG. 3, HL-60 cells were lysed at the indicated times following light treatment. Lysates were subjected to SDS-PAGE, transferred to nitrocellulose and probed with polyclonal (A) anti-CPP32 or (B) anti-PARP antibodies. Lane 1 shows untreated cells; lane 2 shows BPD-treated cells (without light); and lanes 3–7 show BPD and light (complete PDT)treated cells. The results establish that PDT induced the cleavage of CPP32 into its p12 and p17 subunits.

Figure 4A:
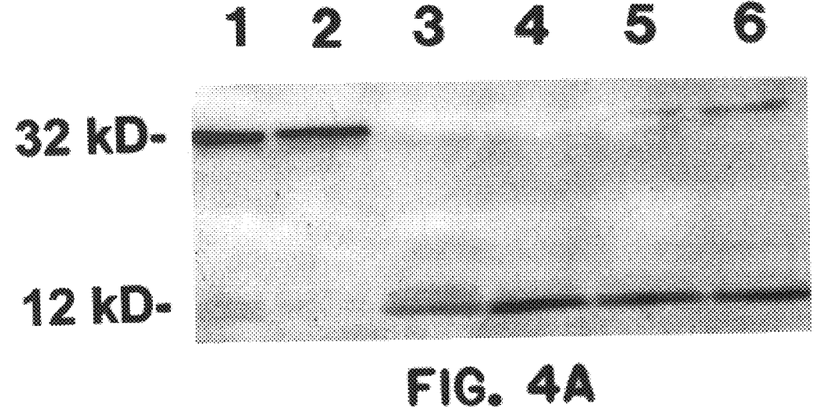
FIG. 4 shows the inhibition by Z-Asp-DCB of the proteolytic cleavage of PARP, but not of CPP32.
Figure 4B:
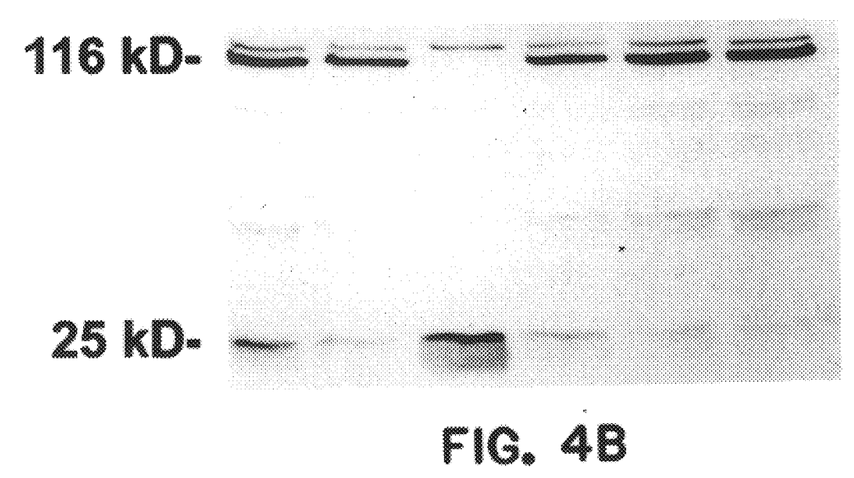
Figure 5A:
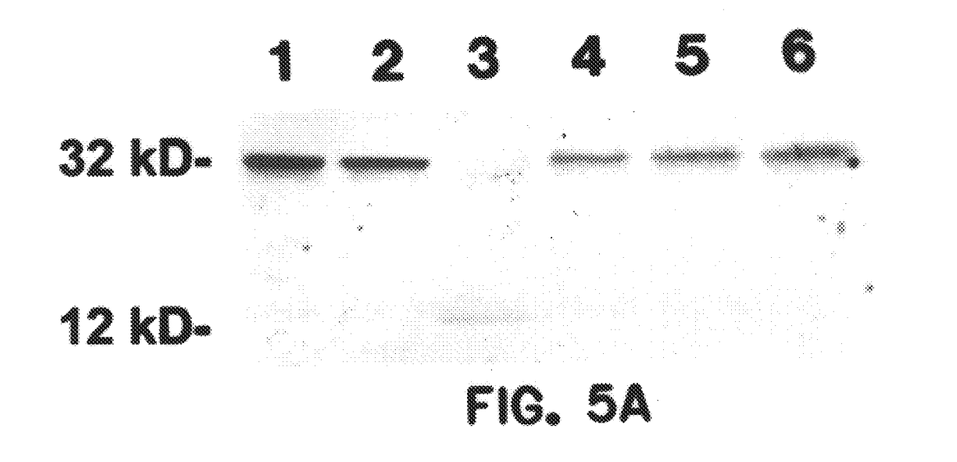
FIG. 5 shows the inhibition by TLCK of proteolytic cleavage of CPP32 and PARP.
Figure 5B:
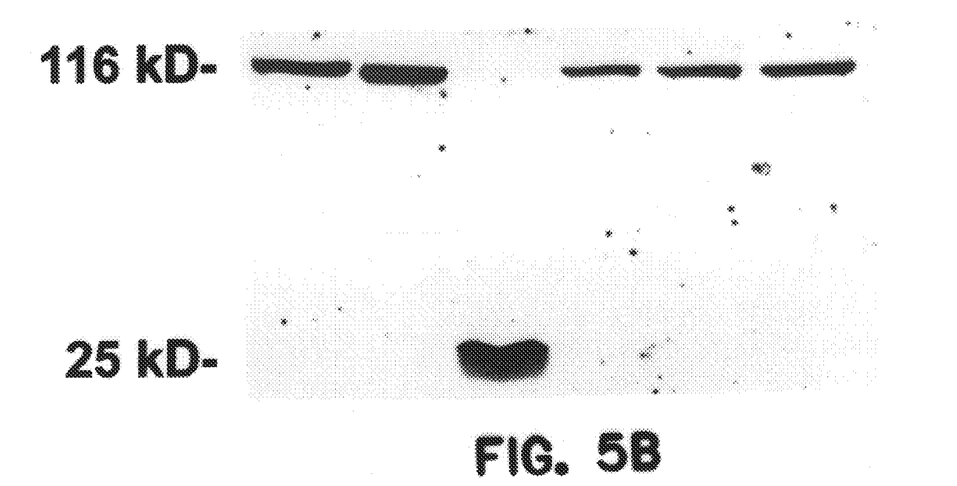

In contrast, the peptide inhibitor Z-Asp-DCB did not block the cleavage of CPP32, as shown in FIG. 4A. In FIG. 4, HL-60 cells were lysed 60 minutes after light exposure. The resulting lysates were subjected to SDS-PAGE, transferred to nitrocellulose, and probed with either polyclonal (A) anti-CPP32 or (B) anti-PARP antibodies. Lane 1 shows untreated cells; lane 2 shows BPD-treated cells; lane 3 shows complete PDT-treated cells; and lanes 4–6 show PDT-treated cells treated with Z-AspDCB at concentrations of 50 µg/mL, 100 µg/mL or 200 µg/mL respectively. The results showed that the Z-Asp-DCB was able to block the cleavage of PARP, a specific substrate of the CPP32 protease, as shown in FIG. 4B. Significantly, the serine protease inhibitor TLCK blocked the cleavage of CPP32, as well as PARP, as shown in FIG. 5.

Figure 7:
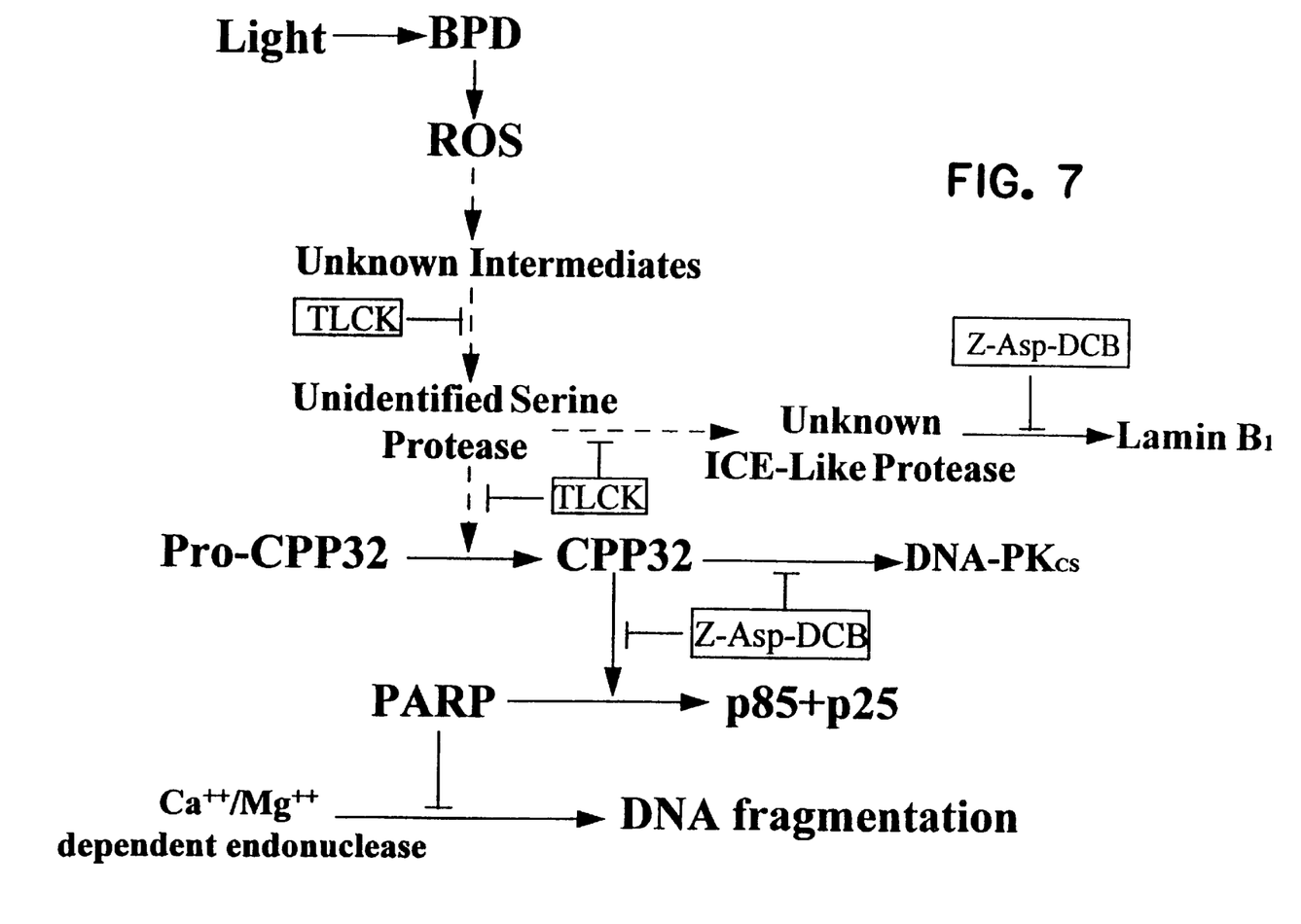
FIG. 7 shows a proposed model for PDT-mediated apoptosis.

Thus, without wishing to be bound by any theory, it is postulated that PARP cleavage is blocked directly by Z-Asp-DCB and indirectly via the cessation of CPP32 action by TLCK. Perhaps the serine protease inhibitor TLCK was able to block apoptosis by interfering with the proteolytic processing of CPP32 by disrupting the activity or processing of an unknown serine protease, as shown in FIG. 7. Following photodynamic treatment of cells containing BPD, reactive oxygen species are rapidly generated. Within 15 minutes, the reactive oxygen species may trigger an unidentified target, perhaps an unidentified serine protease. This serine protease may then cleave ProCPP32 to convert it to active CPP32. TLCK could inhibit this step by directly or indirectly blocking the cleavage of CPP32. Upon CPP32 activation, PARP (p116) would be cleaved into 85 kD and 25 kD fragments.

Figure 6A:
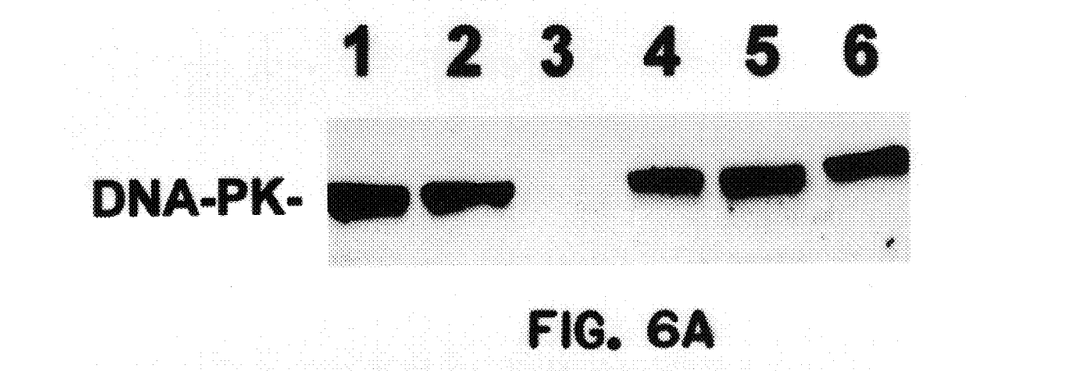
FIG. 6 shows the inhibition by Z-Asp-DCB and TLCK of proteolytic cleavage of DNA-$PK_{CS}$ and lamin $B_1$.

The nuclear-associated proteins, DNA-$PK_{CS}$ and lamin $B_1$, were also cleaved following PDT. However, cleavage of these proteins was disrupted by Z-Asp-DCB, TLCK, or iodoacetamide, as shown in FIG. 6. In FIG. 6, PDT-treated HL-60 cells were lysed 60 minutes after light exposure. The resulting lysates were subjected to SDS-PAGE, transferred to nitrocellulose, and probed with either (A) polyclonal anti-DNA-$PK_{CS}$ or (B) monoclonal anti-lamin $B_1$ antibodies. It is possible that DNA-$PK_{CS}$ is also cleaved by CPP32. With PARP cleavage, the negative regulation of the $Ca^{++}$/$Mg^{++}$-dependent endonucleases would be eliminated, and DNA fragmentation would proceed. In photodynamically-treated cells, lamin $B_1$ was also cleaved by an ICE-like protease.

Figure 6B:
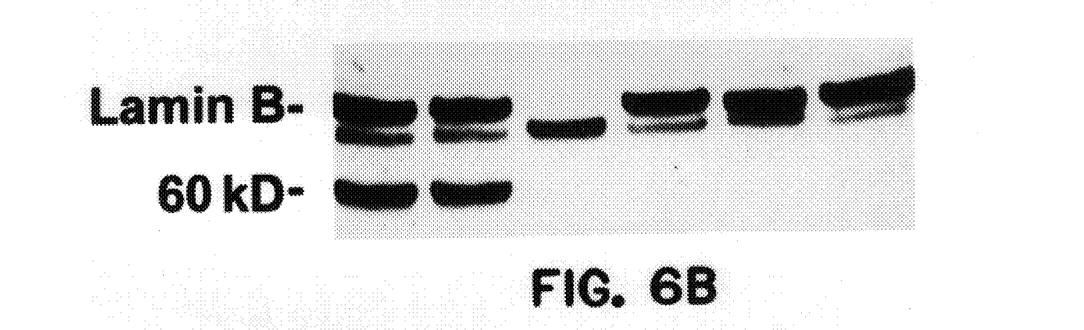

The complete cleavage of a protein ~60–66 kD in cells treated with BPD-MA and light was also detected with the anti-lamin-B1 antibody. Cleavage of the ~60–66 kD protein was not blocked by any of the inhibitors, as shown in FIG. 6B. Lane 1 of FIG. 6 shows untreated cells; lane 2 shows BPD-only treated cells; lane 3 shows PDT-treated cells; lane 4 shows PDT-treated cells that have also been treated with Z-Asp-DCB (200 µg/mL); lane 5 shows PDT-treated cells treated with TLCK (100 µg/mL); and lane 6 shows PDT-treated cells treated with iodoacetamide (500 µg/mL).

What is clamed is:

1. A method for inhibiting apoptosis induced by photodynamic therapy, or decreasing the rate or extent of said apoptosis, in living cells, said method comprising the steps of i) contacting said living cells with a photosensitizing agent and an apoptosis-regulating amount of at least one cysteine or serine protease inhibitor that:

a) inhibits the conversion of the pro-enzyme form of CPP32 to its enzymatically-active form;

b) blocks the proteolytic action of activated CPP32 against its cellular substrates; or c) both, and ii) inducing apoptosis by photodynamic therapy.

2. The method of claim 1 wherein said cysteine protease inhibitor is an interleukin 1β-converting enzyme inhibitor.

3. The method of claim 2 wherein said interleukin 1β-converting enzyme inhibitor is Z-Asp-2,6-dichlorobenzoyloxymethylketone.

4. The method of claim 2 wherein said cysteine protease inhibitor is N-ethylmaleimide or iodoacetamide.

5. The method of claim 1 wherein said compound is a serine protease inhibitor.

6. The method of claim 1 wherein said serine protease inhibitor is 3,4-dichloroisocoumarin or N-tosyl-lysine chloromethyl ketone.

7. The method of claim 1 wherein said living cells are contacted with said cysteine or said serine protease inhibitor prior to being exposed with light in the presence of a photosensitizing agent.

* * * * *